United States Patent
Noshi et al.

(10) Patent No.: US 9,240,045 B2
(45) Date of Patent: Jan. 19, 2016

(54) IMAGE DIAGNOSIS DEVICE AND CONTROL METHOD THEREOF

(71) Applicants: Kabushiki Kaisha Toshiba, Minato-Ku (JP); Toshiba Medical Systems Corporation, Otawara (JP)

(72) Inventors: Yasuhiro Noshi, Otawara (JP); Satoru Nakanishi, Utsunomiya (JP)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 59 days.

(21) Appl. No.: 14/194,183

(22) Filed: Feb. 28, 2014

(65) Prior Publication Data

US 2014/0177934 A1 Jun. 26, 2014

Related U.S. Application Data

(63) Continuation of application No. PCT/JP2013/066881, filed on Jun. 19, 2013.

(30) Foreign Application Priority Data

Jun. 20, 2012 (JP) ................................ 2012-139137

(51) Int. Cl.
*G06K 9/00* (2006.01)
*G06T 7/00* (2006.01)
(Continued)

(52) U.S. Cl.
CPC ................. *G06T 7/0012* (2013.01); *A61B 6/03* (2013.01); *A61B 6/032* (2013.01); *A61B 6/037* (2013.01); *A61B 6/0407* (2013.01);
(Continued)

(58) Field of Classification Search
None
See application file for complete search history.

(56) References Cited

U.S. PATENT DOCUMENTS 5,367,552 A * 11/1994 Peschmann ...................... 378/57
5,838,765 A * 11/1998 Gershman et al. ............ 378/196
(Continued)

FOREIGN PATENT DOCUMENTS

| CN | 1572256 A | 2/2005 |
|---|---|---|
| CN | 101879069 A | 11/2010 |

(Continued)

OTHER PUBLICATIONS

Martinez-Möller, Axel, et al. "Tissue classification as a potential approach for attenuation correction in whole-body PET/MRI: evaluation with PET/CT data." Journal of nuclear medicine 50.4 (2009): 520-526.*

(Continued)

*Primary Examiner* — Bhavesh Mehta
*Assistant Examiner* — Sean Conner
(74) *Attorney, Agent, or Firm* — Oblon, McClelland, Maier & Neustadt, L.L.P.

(57) ABSTRACT

An image diagnosis device comprising: a positioning image collection unit configured to collect a positioning image for an object; a weight distribution estimation unit configured to estimate a weight distribution of the object from the collected positioning image; a top board sagging amount estimation unit configured to estimate an amount of sagging of a top board on which the object is placed, from the estimated weight distribution; and an alignment adjustment unit configured to perform alignment for each captured image of the object, based on the estimated amount of sagging of the top board.

10 Claims, 13 Drawing Sheets

(51) Int. Cl.
  *A61B 6/03* (2006.01)
  *A61B 6/04* (2006.01)
  *A61B 6/00* (2006.01)

(52) U.S. Cl.
  CPC ............ *A61B 6/0492* (2013.01); *A61B 6/4417* (2013.01); *A61B 6/5276* (2013.01); *A61B 6/5247* (2013.01)

(56) References Cited

U.S. PATENT DOCUMENTS

| | | | |
|---|---|---|---|
| 6,111,974 A * | 8/2000 | Hiraoglu et al. | 382/100 |
| 6,553,356 B1 * | 4/2003 | Good et al. | 706/15 |
| 6,738,066 B1 * | 5/2004 | Nguyen | 345/474 |
| 7,020,315 B2 * | 3/2006 | Vaisburd et al. | 382/131 |
| 7,215,806 B1 * | 5/2007 | Bechwati et al. | 382/133 |
| 2002/0122575 A1 * | 9/2002 | Vaisburd et al. | 382/131 |
| 2004/0059242 A1 * | 3/2004 | Masuo et al. | 600/547 |
| 2005/0185054 A1 * | 8/2005 | Edwards et al. | 348/169 |
| 2006/0193443 A1 * | 8/2006 | Reger | 378/207 |
| 2007/0003020 A1 * | 1/2007 | Hsieh et al. | 378/207 |
| 2008/0081985 A1 * | 4/2008 | Zheng et al. | 600/407 |
| 2008/0118122 A1 * | 5/2008 | Sirohey et al. | 382/128 |
| 2008/0285825 A1 * | 11/2008 | Zhang et al. | 382/128 |
| 2008/0289106 A1 * | 11/2008 | Beyer et al. | 5/601 |
| 2008/0301872 A1 * | 12/2008 | Fahrig et al. | 5/81.1 R |
| 2009/0003655 A1 * | 1/2009 | Wollenweber | 382/107 |
| 2009/0062693 A1 * | 3/2009 | Woolfson et al. | 600/587 |
| 2009/0139032 A1 * | 6/2009 | Bak | 5/658 |
| 2009/0322330 A1 * | 12/2009 | Adachi et al. | 324/309 |
| 2010/0106423 A1 * | 4/2010 | Graf et al. | 702/19 |
| 2011/0227910 A1 * | 9/2011 | Ying et al. | 345/419 |
| 2014/0135659 A1 * | 5/2014 | Maggi et al. | 600/595 |
| 2014/0289964 A1 * | 10/2014 | Dodd | 5/613 |

FOREIGN PATENT DOCUMENTS

| | | |
|---|---|---|
| JP | 2005-291814 A | 10/2005 |
| JP | 2006-320545 A | 11/2006 |
| JP | 2007-007415 A | 1/2007 |
| JP | 2007-167408 A | 7/2007 |
| JP | 2012-045318 A | 3/2012 |
| WO | WO 2012/063957 A1 | 5/2012 |

OTHER PUBLICATIONS

Ellis, Kenneth J. "Human body composition: in vivo methods." Physiological reviews 80.2 (2000): 649-680.*
International Search Report mailed Aug. 6, 2013 for PCT/JP2013/066881 filed on Jun. 19, 2013 with English Translation.
International Preliminary Report on Patentability and Written Opinion issued Dec. 23, 2014 in PCT/JP2013/066881 (submitting English translation only).
Combined Chinese Office Action and Search Report issued Jun. 16, 2015 in Patent Application No. 201380003054.7 (with English translation of Category of Cited Documents).

* cited by examiner

IMAGE DIAGNOSIS DEVICE AND CONTROL METHOD THEREOF

CROSS-REFERENCE TO RELATED APPLICATION

This application is a Continuation Application of No. PCT/JP2013/66881, filed on Jun. 19, 2013, and the PCT application is based upon and claims the benefit of priority from Japanese Patent Application No. 2012-139137, filed on Jun. 20, 2012, the entire contents of which are incorporated herein by reference.

FIELD

Embodiments of the present invention relate to an image diagnosis device, and a control method thereof.

BACKGROUND

In recent years, a medical image diagnosis device in which a plurality of medical image diagnosis devices are integrated is being put to practical use. Specifically, a device (referred to also as a PET-CT device) in which a PET (Positron Emission Tomography) diagnosis device for performing function diagnosis with respect to biological tissues of an object and an X-ray CT (Computed Tomography) device for imaging morphological information about biological tissues of an object are integrated is being put to practical use.

This PET-CT device is capable of performing PET examination and X-ray CT examination in succession. Accordingly, the PET-CT device is capable of generating a PET image and an X-ray CT image by one device, and of generating a fused image by combining the PET image and the X-ray CT image.

Now, generally, according to such a medical image diagnosis device, a PET gantry (a radiation detection unit) used by the PET diagnosis device and an X-ray CT gantry (an X-ray scanning unit) used by the X-ray CT device are arranged near each other. Furthermore, such a medical image diagnosis device includes a couch having a top board where an object is to lie, and the PET diagnosis device and the X-ray CT device are to share this couch.

Also, according to such a medical image diagnosis device, the PET gantry of the PET diagnosis device and the X-ray CT gantry of the X-ray CT device are sequentially arranged in tandem, and a tunnel portion is provided inside both gantries in such a way as to pass through the PET gantry and the X-ray CT gantry. The couch has the top board inserted in the tunnel portion inside the gantries along the lengthwise direction of the top board.

Accordingly, with such a medical image diagnosis device, the distance from the couch to the radiation detection unit of the PET diagnosis device and the distance from the couch to the X-ray scanning unit of the X-ray CT device are different, and thus, the sinking of the top board (also referred to as the sagging of the top board) due to the weight is different for each capturing position of the gantries. Accordingly, various methods of correcting the sagging of the top board are being studied.

Now, with a medical image diagnosis, device adopting a plurality of capturing methods, capturing is performed according to each capturing method, and the positions (captured positions) indicated by the captured surfaces are different, and the sagging of the top board is different for each captured position. That is, even with the same captured portion, the sagging of the top board due to weight is different for the PET gantry and for the X-ray CT gantry. Also, since the position of the top board is not shown in a PET image of the PET diagnosis device, alignment of the top boards of the captured images becomes difficult at the time of combining a PET image and an X-ray CT image, and it is difficult to generate a highly accurate fused image where the PET image and the X-ray CT image are appropriately combined.

DETAILED DESCRIPTION

An image diagnosis device according to a present embodiment and a control method of the image diagnosis device will be described with reference to the appended drawings.

To solve the above-described problems, the present embodiments provide the image diagnosis device including: a positioning image collection unit configured to collect a positioning image for an object; a weight distribution estimation unit configured to estimate a weight distribution of the object from the collected positioning image; a top board sagging amount estimation unit configured to estimate an amount of sagging of a top board on which the object is placed, from the estimated weight distribution; and an alignment adjustment unit configured to perform alignment for each captured image of the object, based on the estimated amount of sagging of the top board.

As a result, the image diagnosis device of the present embodiment is capable of performing alignment for each captured image based on an estimated amount of sagging of a top board, and thus, alignment of the top board may be appropriately performed, and highly accurate correction with fused captured images may be performed and a fused image may be obtained.

To solve the above-described problems, the present embodiments provide the control method of an image diagnosis device, the method comprising: collecting a positioning image for an object; estimating a weight distribution of the object from the collected positioning image; estimating an amount of sagging of a top board on which the object is placed, from the estimated weight distribution; and performing alignment for each captured image of the object, based on the estimated amount of sagging of the top board.

As a result, the control method of the image diagnosis device according to the present embodiment is capable of performing alignment for each captured image based on an estimated amount of sagging of a top board, and thus, alignment of the top board may be appropriately performed, and highly accurate correction with fused captured images may be performed and a fused image may be obtained.

First Embodiment

In the following, a PET-CT device (image diagnosis device) 100 according to a present embodiment will be described with reference to the appended drawings. Additionally, in the present embodiment, description will be given using a PET-CT device as an example of a device in which a plurality of medical image diagnosis devices adopting different capturing methods are integrated.

Figure 1:
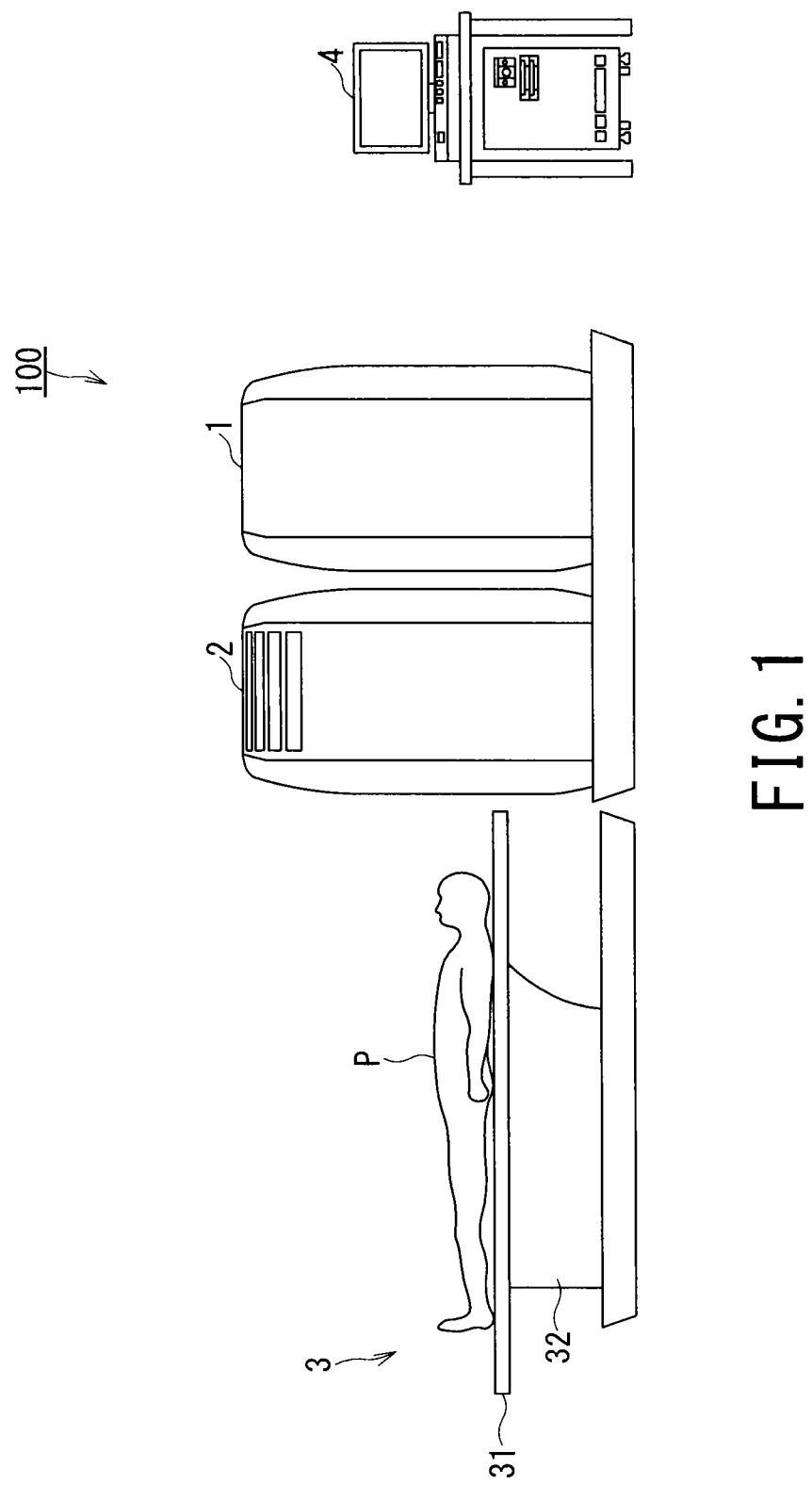
FIG. 1 is a conceptual diagram showing an example configuration of a PET-CT device according to a present embodiment.

FIG. 1 is a schematic configuration diagram showing a schematic configuration of the PET-CT device 100 according to the present embodiment.

As shown in FIG. 1, the PET-CT device 100 is configured including a PET gantry device 1, a CT gantry device 2, a couch device 3, and a console device 4. Additionally, an object P is injected with a radio isotope or a labeled compound thereof.

The PET gantry device 1 is a device for detecting a pair of gamma rays emitted from a living tissue which has taken in a positron-emitting radionuclide injected into the object P, and generating projection data of gamma rays (referred to also as gamma-ray projection data) for reconstructing a PET image. That is, this PET gantry device 1 uses the property of a labeled compound such as a radio isotope to be selectively taken in by a specific tissue or organ in a living body, and measures the gamma ray emitted by the isotope outside the body and images the dose distribution of the radio isotope.

The CT gantry device 2 is a device for radiating X-rays on the object P from the outside the body, detecting X-rays passing through a tissue or an organ of the object P, and generating an X-ray projection data for reconstructing an X-ray CT image. That is, the CT gantry device 2 has a function of imaging a difference in X-ray transmittance at a tissue or an organ or measuring the intensity of an X-ray by a detector, and reconstructing an image based on the value.

The couch device 3 is a bed on which the object P is to lie, and includes a top board 31, and a couch 32. The couch device 3 is moved to a capturing opening of each of the PET gantry device 1 and the CT gantry device 2 according to an instruction of an operator of the PET-CT device 100 received via the console device 4. That is, the PET-CT device 100 moves the couch device 3 according to an instruction from the console device 4, to thereby capture an X-ray CT image or a PET image. Movement of the couch device 3 will now be described.

Figure 2A:
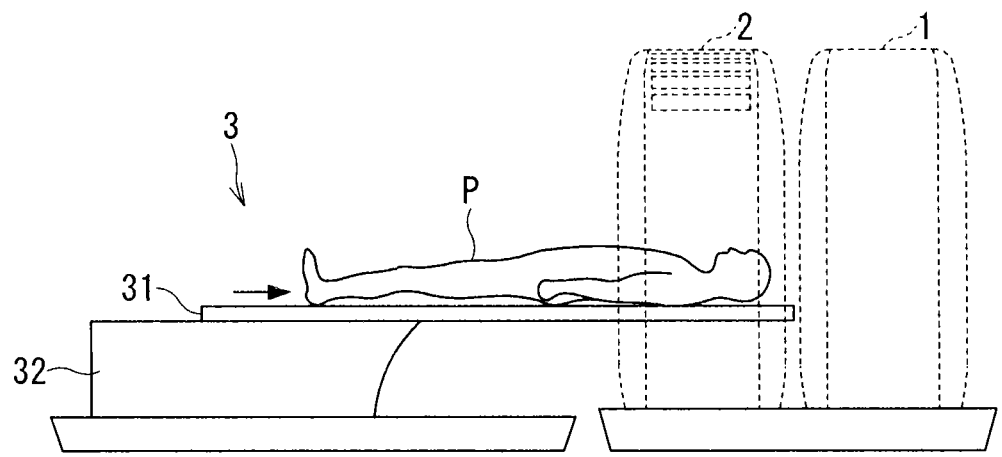
FIGS. 2A and 2B are explanatory diagrams for describing movement of a couch device according to the present embodiment.
Figure 2B:
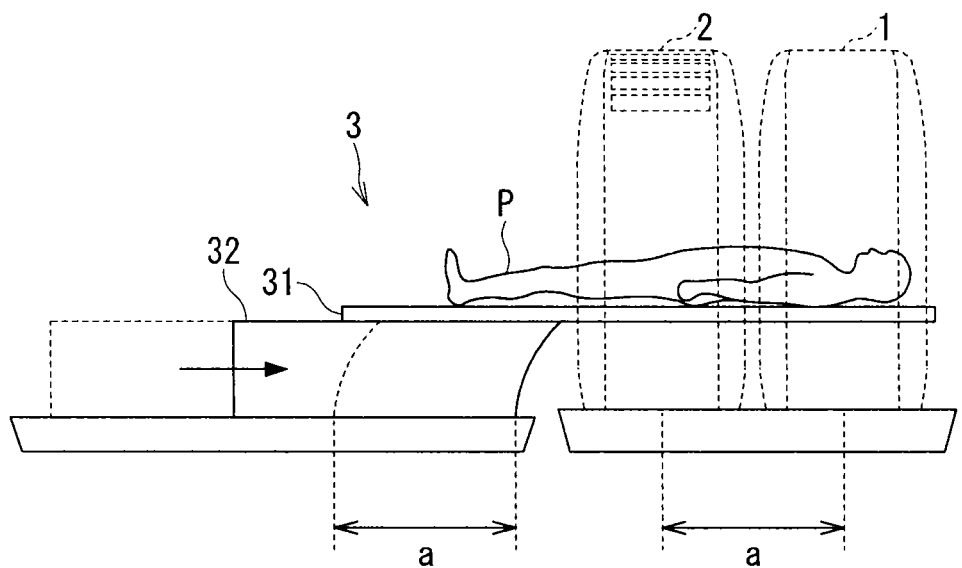

FIGS. 2A and 2B are explanatory diagrams for describing movement of the couch device 3 according to the present embodiment.

As shown in FIGS. 2A and 2B, the console device 4 (FIG. 1) causes the top board 31 and the couch 32 to move along the body axis direction of the object P by a drive mechanism not shown. For example, at the time of capturing an X-ray CT image, the PET-CT device 100 horizontally moves the top board 31 in the direction of the CT gantry device 2, as shown in FIG. 2A. Then, the PET-CT device 100 scans a capturing portion of the object P by a continuous movement method of the top board according to which the top board 31 is horizontally moved (for example, there is a helical scanning method according to which scanning by X-rays is performed spirally and continuously). Then, the CT gantry device 2 captures an X-ray CT image. Additionally, an X-ray is a type of an electromagnetic wave, and has a wavelength of several hundred angstroms to 0.1 angstroms.

Furthermore, after capturing an X-ray CT image, the PET-CT device 100 horizontally moves the couch 32 along the body axis direction with the top board 31 still drawn out from the couch 32, as shown in FIG. 2B. Then, the PET-CT device 100 inserts the capturing portion of the object P into a capturing opening of the PET gantry device 1.

Here, as shown in FIG. 2B, the couch 32 moves the same distance as a distance "a" between center positions of respective detectors of the PET gantry device 1 and the CT gantry device 2. That is, the amount of stroke (the amount of drawing out) from the couch 32 at the time of capturing the same portion of the object P is made the same by the movement of the couch 32 over the distance "a".

At the time of capturing PET images, the PET-CT device 100 captures a part of the object P, then, horizontally moves, in a stepwise manner, the top board 31 by a predetermined movement amount in a state where capturing is stopped, and further captures another part. In this manner, according to the capturing method of repeated movement and capturing (referred to also as a step-and-shoot method), the PET gantry device 1 of the PET-CT device 100 is enabled to capture the object P over a wide range.

The console device 4 shown in FIG. 1 is a device for controlling a capturing process of the PET-CT device 100 according to an instruction from an operator. Here, the configuration of the console device 4 will be described.

Figure 3:
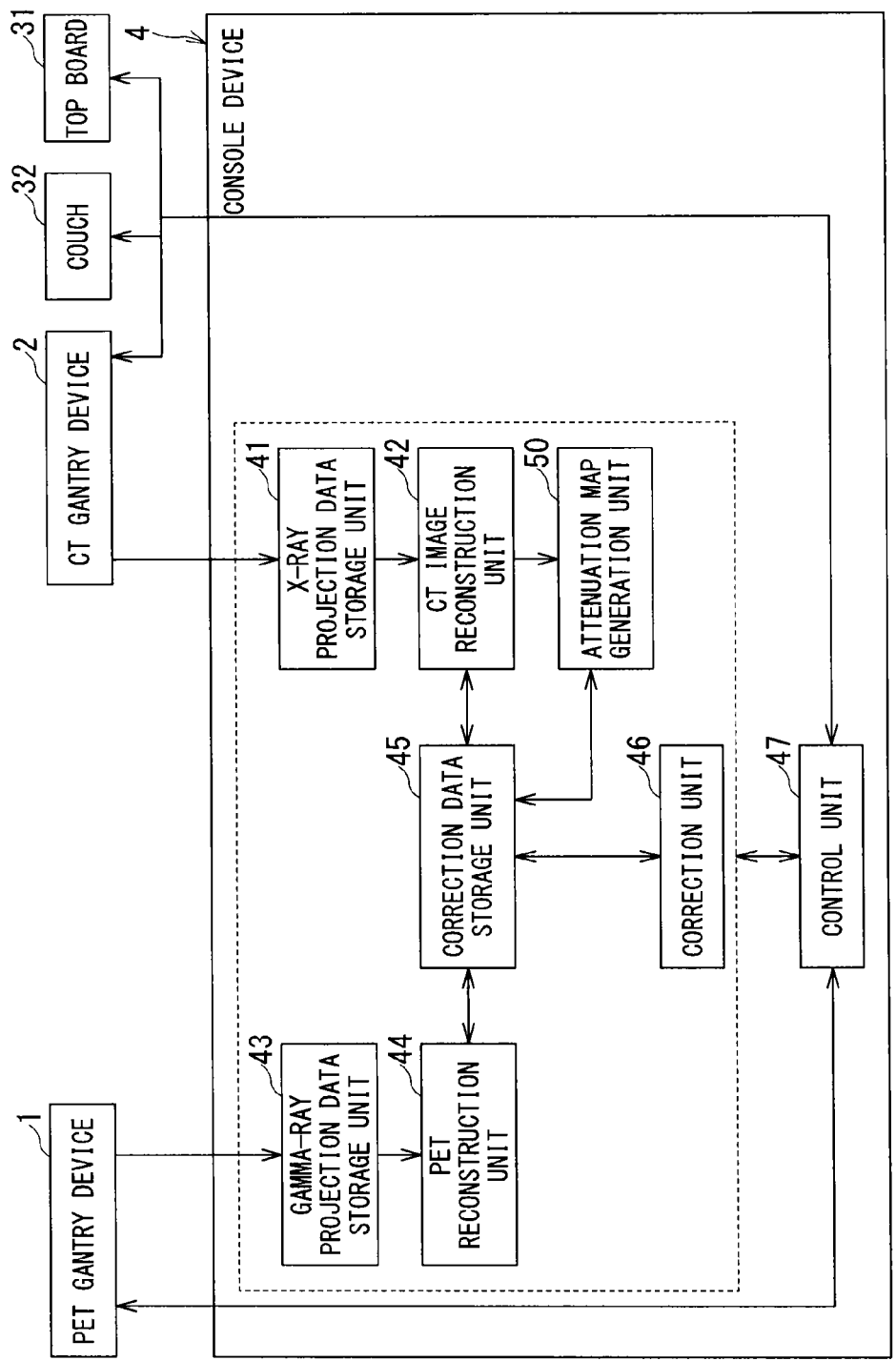
FIG. 3 is a configuration diagram showing a configuration of a console device according to the present embodiment.

FIG. 3 is a configuration diagram showing a configuration of the console device 4 according to the present embodiment.

As shown in FIG. 3, the console device 4 is configured including an X-ray projection data storage unit 41, a CT image reconstruction unit 42, a gamma-ray projection data storage unit 43, a PET reconstruction unit 44, a correction data storage unit 45, an attenuation map generation unit 50, a correction unit 46, and a control unit 47.

The X-ray projection data storage unit 41 stores the X-ray projection data transmitted from the CT gantry device 2. Specifically, the X-ray projection data storage unit 41 stores the X-ray projection data used for reconstructing an X-ray CT image. Also, the X-ray projection data storage unit 41 stores projection data for reconstructing a positioning image (referred to also as a scanogram) for determining a slice position for a slice image before capturing of a slice image. Additionally, the projection data for reconstructing a scanogram is to be transmitted from the CT gantry device 2, as with the X-ray projection data.

The CT image reconstruction unit 42 reconstructs an X-ray CT image by performing a back projection process on the X-ray projection data for reconstruction stored in the X-ray projection data storage unit 41 by a FBP (Filtered Back Projection) method, for example. Specifically, the CT image reconstruction unit 42 reconstructs, from the X-ray projection data, a plurality of X-ray CT images capturing a plurality of cross section images orthogonal to the body axis direction of the object P, based on a capturing condition (for example, a slice width or the like) determined according to a capturing plan in a full body examination using the PET-CT device 100. Also, the CT image reconstruction unit 42 reconstructs a scanogram from the X-ray projection data before reconstructing the X-ray CT image. Then, the CT image reconstruction unit 42 stores the reconstructed scanogram and the X-ray CT image in the correction data storage unit 45.

The gamma-ray projection data storage unit 43 stores the gamma-ray projection data transmitted from the PET gantry device 1.

The PET reconstruction unit 44 reconstructs a PET image by a statistical reconstruction method, for example, from the gamma-ray projection data stored in the gamma-ray projection data storage unit 43. Also, the PET reconstruction unit 44 performs attenuation correction for the PET image using an attenuation map described below. Then, the PET reconstruction unit 44 stores the reconstructed PET image in the correction data storage unit 45.

The correction data storage unit 45 stores X-ray CT images reconstructed by the CT image reconstruction unit 42, scanograms, and PET images reconstructed by the PET reconstruction unit 44. Furthermore, the correction data storage unit 45 also stores a database of the amount of top board sagging indicating a curve of the amount of top board sagging. Additionally, details of this database of the amount of top board sagging will be given below.

The attenuation map generation unit 50 generates an attenuation map (μ Map) for correcting the attenuation of gamma rays occurring inside the body of the object P, using the X-ray CT image reconstructed by the CT image reconstruction unit 42. Additionally, the attenuation map is obtained by converting pixel values from the X-ray CT image. Also, the attenuation map generation unit 50 corrects the attenuation map in advance based on the amount of correction for top board sagging described below, in such a way that the height of the top board coincides between the PET image and the X-ray CT image. Then, the attenuation map generation unit 50 stores the corrected attenuation map in the correction data storage unit 45.

The correction unit 46 reads the scanograms, the X-ray CT images and the PET images stored in the correction data storage unit 45, and also, reads the database of the amount of top board sagging stored in the correction data storage unit 45. The correction unit 46 corrects a PET image on which attenuation correction has been performed by the PET reconstruction unit 44 to the position of the X-ray CT image. The correction unit 46 generates a fused image with the X-ray CT image after correcting the position of the PET image on which attenuation correction has been performed, based on the estimated amount of correction for top board sagging described below. Details of this correction unit 46 will be given below.

The control unit 47 controls the overall operation of the PET-CT device 100. Specifically, the control unit 47 controls the capturing process by the PET-CT device 100 by controlling the operation of the PET gantry device 1, the CT gantry device 2, the top board 31 and the couch 32.

For example, the control unit 47 controls the process of reconstruction by the CT image reconstruction unit 42, using the X-ray projection data for X-ray reconstruction stored in the X-ray projection data storage unit 41. Also, the control unit 47 controls the process of reconstruction or attenuation correction by the PET reconstruction unit 44, using the gamma-ray projection data stored in the gamma-ray projection data storage unit 43. Moreover, the control unit 47 controls the correction process by the correction unit 46, and also, controls a display unit, not shown, to display a fused image, by receiving an instruction of an operator from an input/output device, not shown.

Additionally, the control unit 47 is configured from a CPU (Central Processing Unit), a ROM (Read Only Memory), a RAM (Random Access Memory) and the like that are not shown.

The CPU loads various programs stored in the ROM on the RAM, and develops the programs, to thereby realize the functions of the various programs. The RAM is used as a work area (a working memory). The ROM stores various programs. The various programs stored in the ROM include programs for realizing each capturing process, each reconstruction process, the attenuation correction, the correction process by the correction unit 46, and the like.

Next, a deviation between images captured by the PET gantry device 1 by the step-and-shoot method and captured by the CT gantry device 2 by the helical scanning method will be described.

Figure 4:
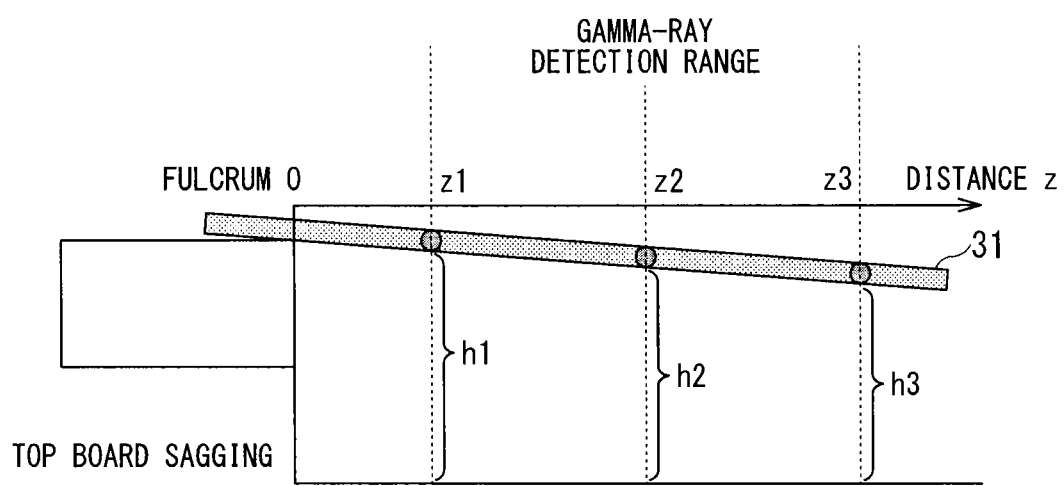
FIG. 4 is an explanatory diagram for describing a capturing range, including the sagging of a top board, from a fulcrum of the top board until a gamma-ray detection range where a PET gantry device according to the present embodiment detects a gamma ray.

FIG. 4 is an explanatory diagram for describing a capturing range, including the sagging of the top board, 31, from a fulcrum 0 of the top board 31 until a gamma-ray detection range where the PET gantry device 1 according to the present embodiment detects a gamma ray.

As shown in FIG. 4, the PET gantry device 1 detects gamma rays in the capturing range from a distance $z_1$ to a distance $z_3$ with a distance $z_2$ at the center. In this drawing, a height h of the top board 31 indicates that a height $h_2$ of the top board 31 at the capturing position at the distance z2 is lower than a height h1 of the top board 31 at the capturing position at the distance z1, and that a height h3 of the top board 31 at the capturing position at the distance z3 is lower than the heights of the top board 31 at the capturing positions at the distances z1 and z2. Additionally, the distance z1 to the distance z3 indicate the amounts of stroke of the top board 31 from the fulcrum 0. Also, the fulcrum 0 is an arbitrary reference position used as the reference for the amount of stroke.

As described, FIG. 4 shows that the farther away the capturing position of the top board 31 from the fulcrum 0 of the top board 31, the more the top board 31 is deflected downward on the page. Additionally, the sagging of the top board 31 (a state where the top board 31 is sunken) may be expressed as the top board sagging, and the amount of sagging of the top board 31 may be expressed as the amount of top board sagging. Accordingly, this top board sagging may also be expressed as the height h of the top board 31.

Figure 5A:
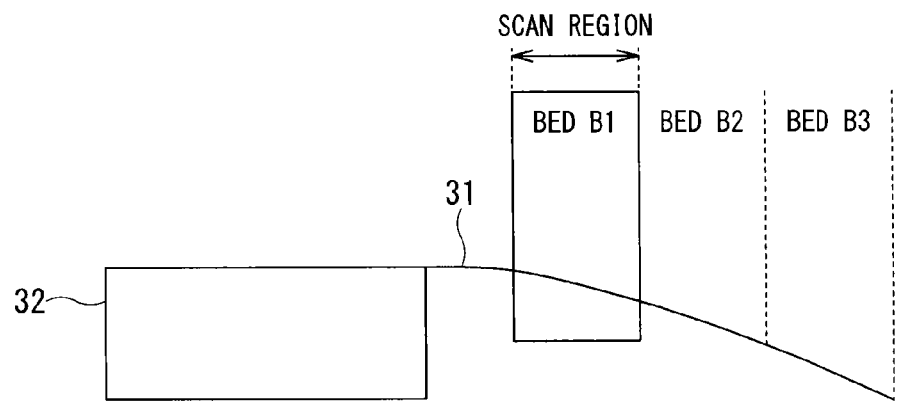
FIGS. 5A to 5C are explanatory diagrams for describing top board sagging in a captured image captured by a step-and-shoot method by the PET gantry device according to the present embodiment.
Figure 5B:
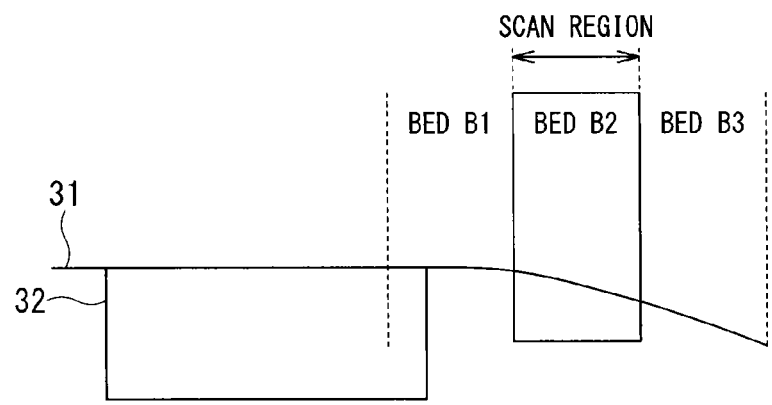
Figure 5C:
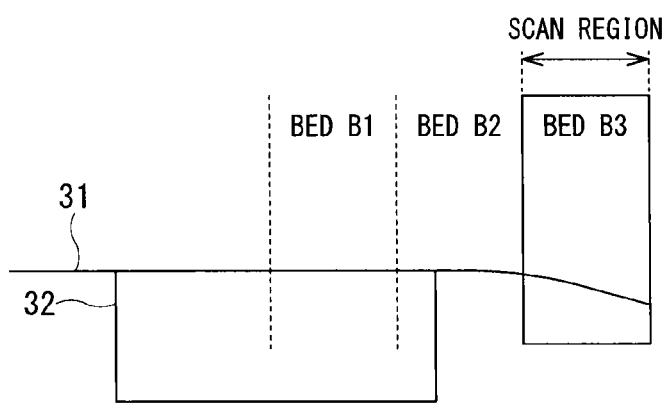

FIGS. 5A to 5C are explanatory diagrams for describing the top board sagging in a captured image captured by the step-and-shoot method by the PET gantry device 1 according to the present embodiment. Additionally, a capturing region of a PET image is described as a scan region. Also, beds B1, B2 and B3 shown in FIGS. 5A to 5C indicate the capturing positions of PET images (the capturing range). Moreover, in the drawings of FIGS. 5A to 5C, the object P is not shown, but the top board sagging of a case where the object P is placed on the top board 31 is actually shown.

As shown in FIGS. 5A to 5C, the amount of top board sagging is different depending on the amount of stroke by which the top board 31 is drawn out from the couch 32. For example, as shown in FIG. 5A, in the case of performing scanning at the position of the bed B1 in a state where the top board 31 is drawn out from the couch 32, the load (the weight) of the object P greatly affects the top board 31, and the amount of top board sagging in the scan region is great.

On the other hand, as shown in FIGS. 5B and 5C, when the amount of stroke by which the top board 31 is drawn out is reduced, the influence exerted by the load (the weight) of the object P on the top board 31 is reduced, and the amount of top board sagging in the scan region becomes small. That is, as shown in FIG. 5B, in the case of performing scanning at the position of the bed B2, the amount of top board sagging of the top board 31 is smaller than the amount of top board sagging in the case of performing scanning at the position of bed B1. Also, as shown in FIG. 5C, in the case of performing scanning at the position of bed B3, the amount of top board sagging of the top board 31 is smaller than the amount of top board sagging in the case of performing scanning at the position of bed B1 or B2.

Figure 6:
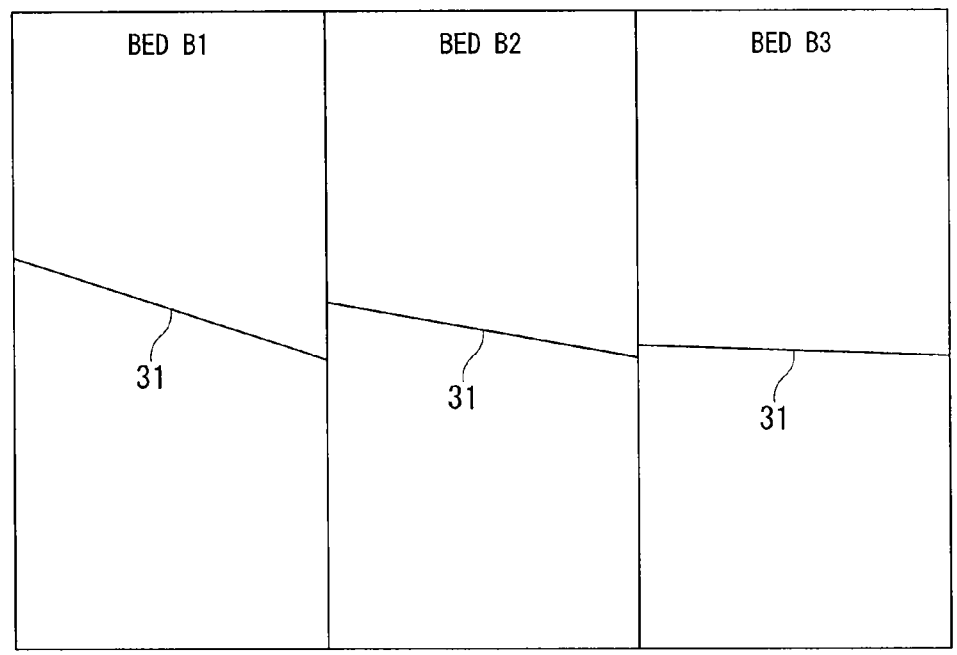
FIG. 6 is an explanatory diagram for describing the position of the top board in the case of the PET gantry device according to the present embodiment capturing an object by the step-and-shoot method.

FIG. 6 is an explanatory diagram for describing the position of the top board 31 where the object P is captured by the step-and-shoot method by the PET gantry device 1 according to the present embodiment. Additionally, the position of the top board 31 indicates the height and inclination of the top board 31 at a capturing position.

In FIG. 6, the cross sections of the object P along the body axis direction at the time of the PET gantry device 1 capturing the top board 31 at the positions of the beds B1, B2 and B3 are shown. That is, it is shown that, when the PET gantry device 1 captures the object P by the step-and-shoot method, the amount of top board sagging is different for each capturing position of the bed, and thus, there is a difference in the level of the top board 31 between the beds. Next, the position of the top board 31 in the case of the CT gantry device 2 capturing the object P by the helical scanning method will be described.

Figure 7:
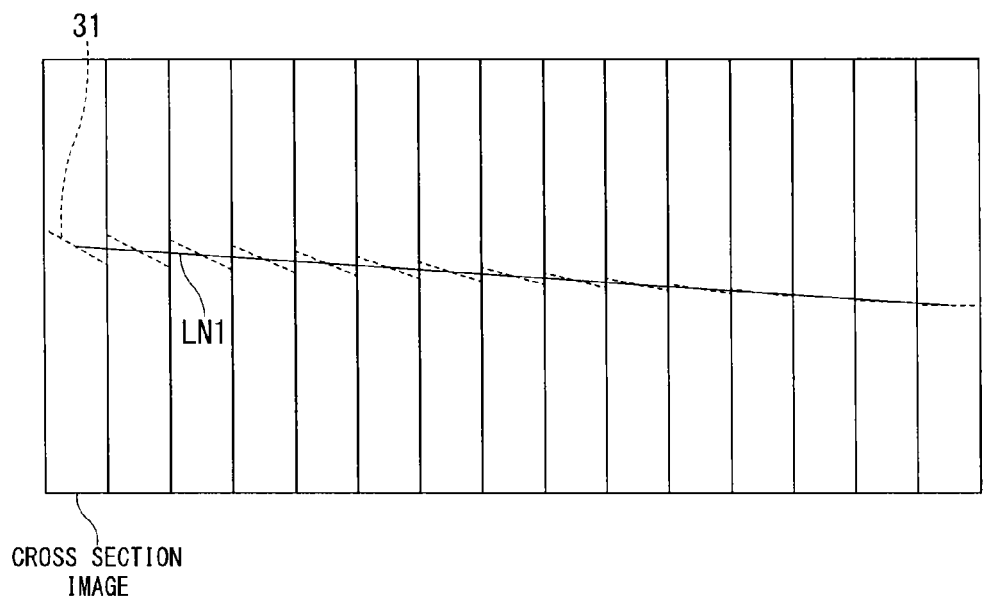
FIG. 7 is an explanatory diagram for describing the position of the top board in the case of a CT gantry device according to the present embodiment capturing an object by a helical scanning method.

FIG. 7 is an explanatory diagram for describing the position of the top board 31 in the case of the CT gantry device 2 according to the present embodiment capturing the object P by the helical scanning method.

In FIG. 7, the cross sections of the top board 31 along the body axis direction at the time of the CT gantry device 2 successively capturing the top board 31 by the helical scanning method are shown. That is, the cross sections of the top board 31 along the body axis direction are shown using a plurality of cross section images captured by the CT gantry device 2 capturing the top board 31 by the helical scanning method. Additionally, the rectangles shown in FIG. 7 are slice widths of the cross section images. Also, a straight line LN1 shown in FIG. 7 shows a straight line passing through the center of the top board 31 in each cross section image.

In the case of the CT gantry device 2 capturing the object P by the helical scanning method, the amount of top board sagging of the top board 31 becomes great in accordance with the increase in the amount of stroke of the top board 31, and thus, the height of the top board 31 in the cross section images gradually becomes lower in accordance with the increase in the amount of stroke of the top board 31.

Here, the height of the top board 31 where the X-ray CT image captured by the helical scanning method is seen in the body axis direction is the straight line LN1 passing through the center of the top board 31. Next, a positional deviation between a captured image captured by the step-and-shoot method and a captured image captured by the helical scanning method will be described.

Figure 8:
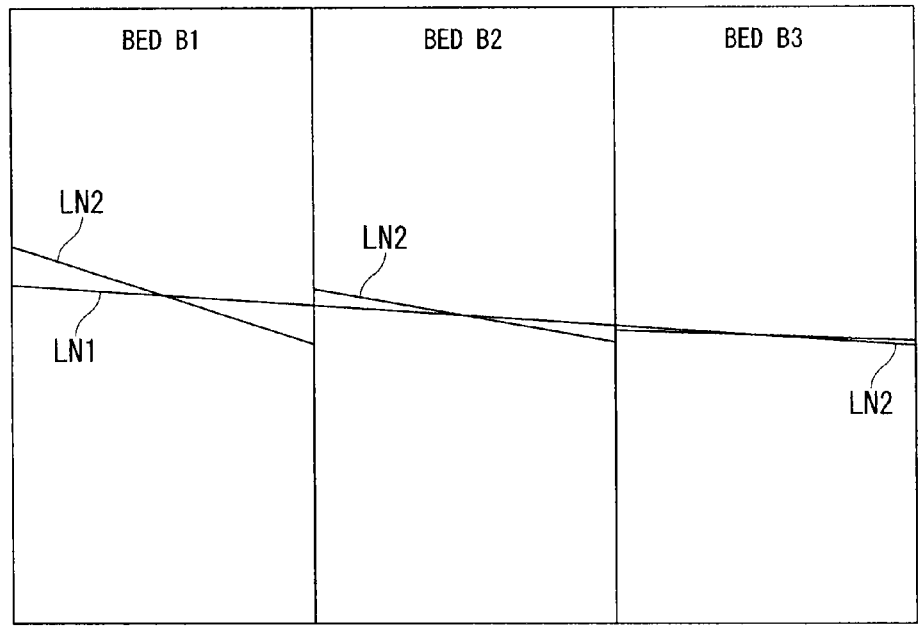
FIG. 8 is an explanatory diagram for describing a positional deviation between a captured image captured by the step-and-shoot method and a captured image captured by the helical scanning method.

FIG. 8 is an explanatory diagram for describing a positional deviation between a captured image captured by the step-and-shoot method and a captured image captured by the helical scanning method.

In FIG. 8, the position of the top board 31 in the captured image captured by the step-and-shoot method shown in FIG. 6 (shown by a straight line LN2), and the position of the top board 31 in the captured image captured by the helical scanning method shown in FIG. 7 (the straight line LN1 described above) are shown.

As shown by the straight lines LN1 and LN2 in FIG. 8, the inclination of the top board 31 is different depending on the capturing method, and it is shown that the positions of the captured images are deviated from each other. That is, this positional deviation of the top board 31 causes a shift between images at the time of fusing the PET image and the X-ray CT image, thereby making it difficult to perform highly accurate correction or to obtain a fused image.

Accordingly, the PET-CT device 100 according to the first embodiment is enabled to estimate, by the correction unit 46 described above, the weight distribution of the object P from the scanogram image (positioning image) at the time of capturing the X-ray CT image and estimate the amount of top board sagging, and to perform a correction process for a captured image.

The PET-CT device 100 is thereby enabled to align the X-ray CT image and the PET image based on the estimated amount of top board sagging, and thus, the alignment of the top board 31 may be performed appropriately, and highly accurate correction with fused PET image and X-ray CT image may be performed and a fused image may be obtained.

As described above, the PET-CT device 100 according to the present embodiment is capable of estimating the amount of top board sagging of the top board 31 from a scanogram in which the top board 31 is not shown, and thus, an X-ray CT image showing the top board 31 is not necessary, and also, a captured image may be corrected without actually measuring the amount of top board sagging of the top board 31.

Next, the correction unit 46 of the console device 4 of the PET-CT device 100 will be described.

Figure 9:
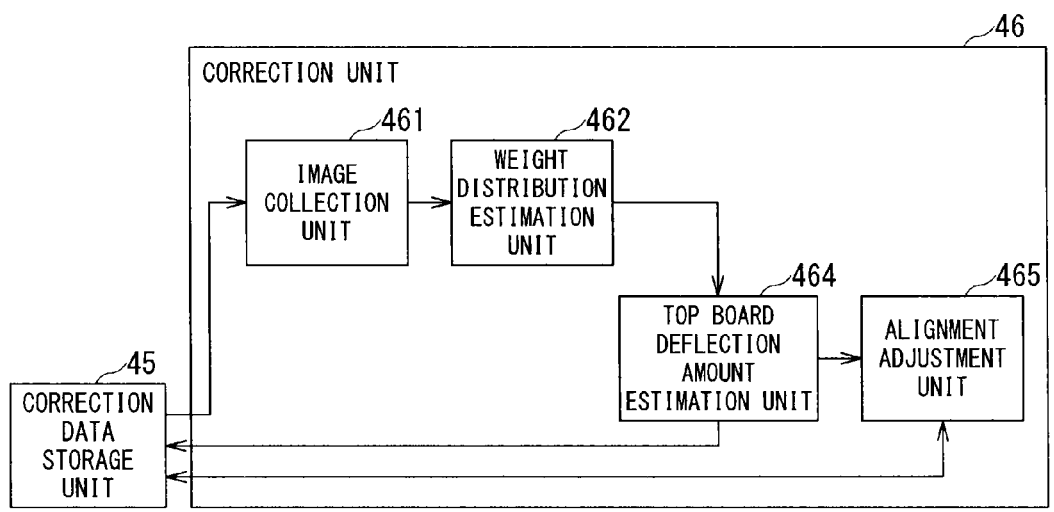
FIG. 9 is a functional block diagram showing a configuration of a correction unit of a console device of the PET-CT device according to the present embodiment.

FIG. 9 is a functional block diagram showing a configuration of the correction unit 46 of the console device 4 of the PET-CT device 100 according to the present embodiment.

As shown in FIG. 9, the correction unit 46 is configured including an image collection unit 461, a weight distribution estimation unit 462, a top board sagging amount estimation unit 464, and an alignment adjustment unit 465. Also, the correction unit 46 is connected to the correction data storage unit 45.

The image collection unit 461 collects a scanogram of the object P from the correction data storage unit 45.

The weight distribution estimation unit 462 estimates the weight distribution of the object P from the scanogram collected by the image collection unit 461. Here, a method of estimating the weight distribution of the object P from the scanogram will be described with reference to the drawings.

Figure 10:
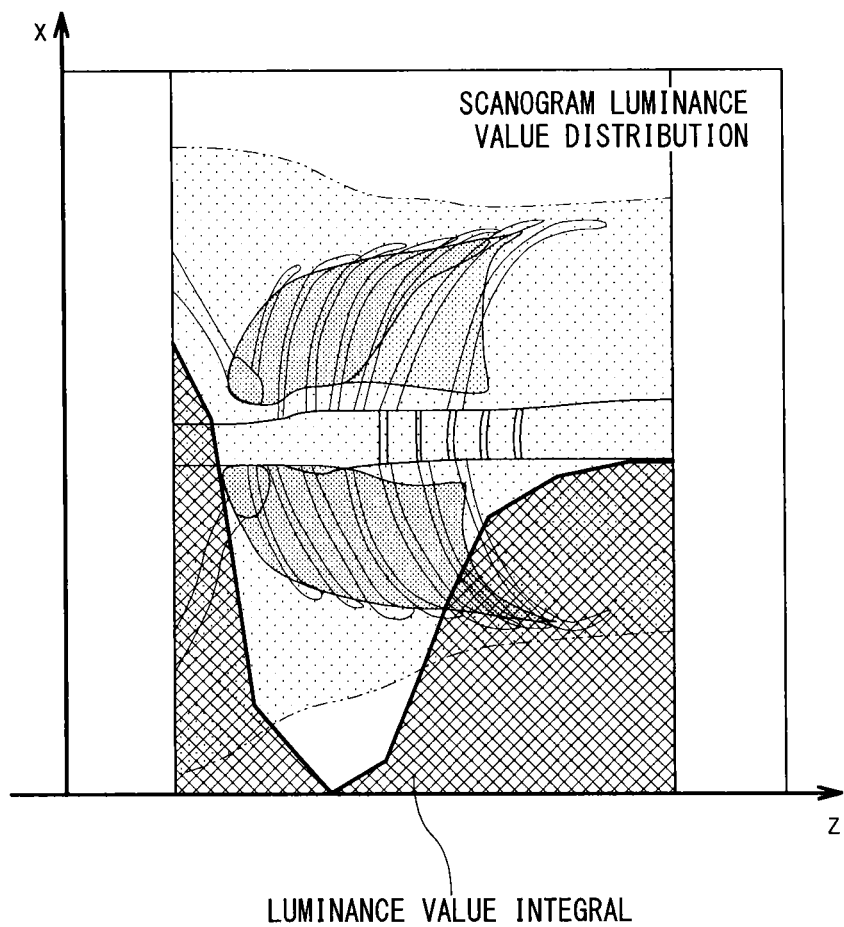
FIG. 10 is an explanatory diagram showing an example of an estimation method of estimating a weight distribution of an object from a scanogram of the object by a weight distribution estimation unit of the present embodiment.

FIG. 10 is an explanatory diagram showing an example of an estimation method of estimating the weight distribution of the object P from the scanogram of the object P by the weight distribution estimation unit 462 according to the present embodiment.

In FIG. 10, a scanogram of the object P is displayed. Also, with respect to the part shown as the scanogram, the shoulders of the object P are positioned at the left end of FIG. 10, and lungs, organs and the like are displayed in the rightward direction on the page. Also, a luminance value integral shown in FIG. 10 indicates the density (the degree of concentration) of tissues of organs, bones and the like of the object P. That is, the luminance value integral shows the distribution of the body weight of the object P.

The weight distribution estimation unit 462 obtains the luminance value integral from the scanogram, calculates the water equivalent thickness of the object P from the luminance value integral, and generates a water equivalent thickness profile for each body axis. The weight distribution estimation unit 462 estimates the weight distribution of the object P from an AUC (Area Under Curve) of the water equivalent thickness profile generated.

Additionally, the water equivalent thickness profile is generated from the luminance value integral, but this is not restrictive, and the body thickness may be calculated from the pixel values of the scanogram and the diameter of the water phantom, and the water equivalent thickness may be estimated from the body thickness. The water equivalent thickness profile here is an analysis result or analysis information obtained by analyzing the body weight for each body axis. Also, the AUC is the area under the curve of the water equivalent thickness profile, and is the area of the portion surrounded by the horizontal axis indicating the zero value of the vertical axis and the curve.

Figure 11:
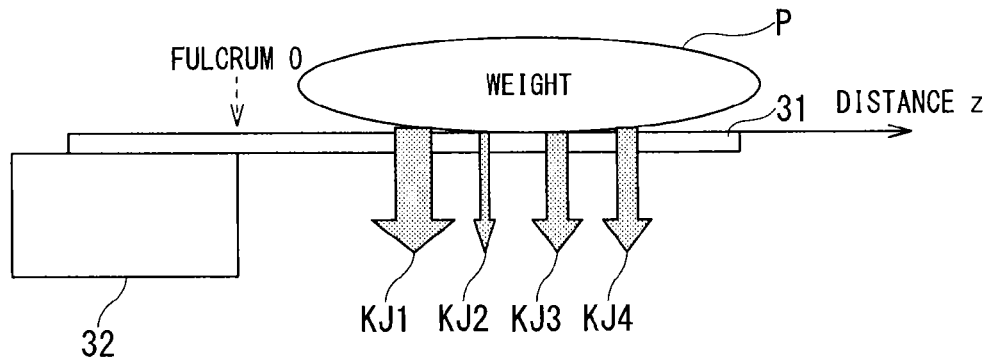
FIG. 11 is an explanatory diagram showing a state where, in a state where an object is on the top board, the weight of the object is distributed over four points.

FIG. 11 is an explanatory diagram showing a state where, in a state where the object P is on the top board 31, the weight of the object P is distributed over four points.

As shown in FIG. 11, the weight is distributed over four points (four parts) on the top board 31. Specifically, from the side of the fulcrum 0, weight KJ1, weight KJ2, weight KJ3 and weight KJ4 are distributed on the top board 31. Additionally, this distribution of the weight is only an example, and four points is not restrictive, and any weight distribution may be estimated from the luminance value integral or the water equivalent thickness profile. Also, the weight distribution may be estimated taking into account sex, age or the like of the object P.

The top board sagging amount estimation unit 464 (FIG. 9) estimates the amount of top board sagging (the amount of sagging) of the top board 31 on which the object P is placed, from the weight distribution estimated by the weight distribution estimation unit 462 (FIG. 9). The top board sagging amount estimation unit 464 may use any calculation method to estimate the amount of top board sagging. For example, it is possible to use the method of calculating the "amount of bending in a beam", which is a known art, and estimate (calculate) the amount of top board sagging of the top board 31 from the distance between the fulcrum of the top board 31 and a capturing position, the position of a support portion, the weight position, the weight distribution or the like. Here, a relationship between movement of the top board position of the top board 31 and a scan position will be described with reference to the drawings.

Figure 12:
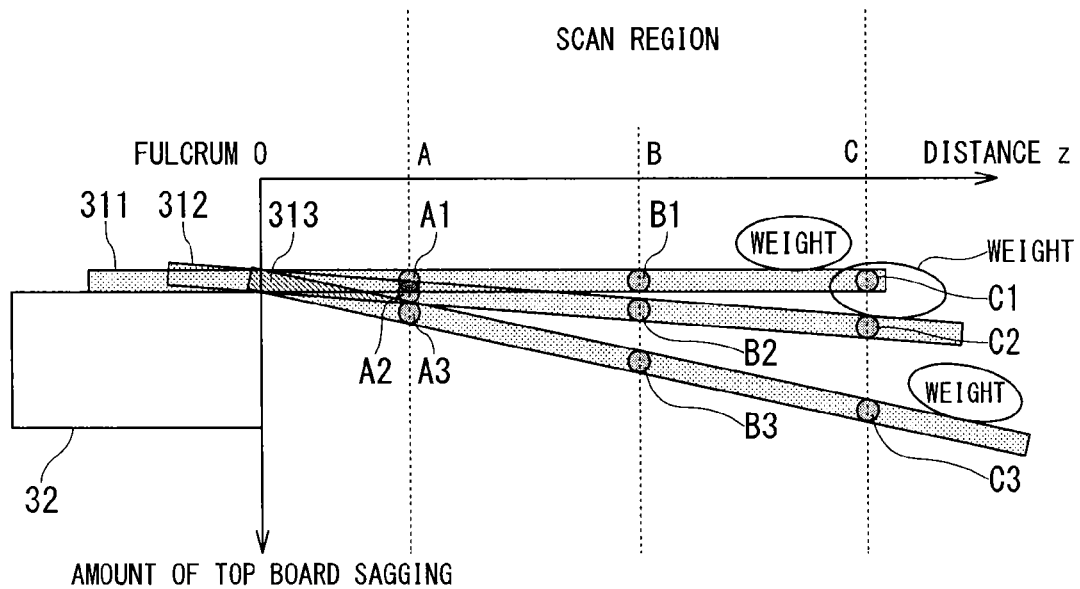
FIG. 12 is an explanatory diagram for describing, with respect to the top board, a relationship between a change in distance from the fulcrum to a capturing position and the amount of top board sagging at a corresponding capturing position.

FIG. 12 is an explanatory diagram for describing, with respect to the top board 31, a relationship between a change in distance from the fulcrum 0 to a capturing position and the amount of top board sagging at a corresponding capturing position.

FIG. 12 shows movement of the top board 31 in the range from a top board position 311 to a top board position 313 based on the amount of stroke of the top board 31. Specifically, in the case the position of the top board 31 is at the top board position 311, the top board 31 is positioned such that a capturing position A1 to a capturing position C1, with a capturing position B1 at the center, is given as the scan region.

On the other hand, in the case the position of the top board 31 is at the top board position 312, the top board 31 is positioned such that a capturing position A2 to a capturing position C2, with a capturing position B2 at the center, is given as the scan region. Moreover, in the case the position of the top board 31 is at the top board position 313, the top board 31 is positioned such that a capturing position A3 to a capturing position C3, with a capturing position B3 at the center, is given as the scan region.

As is clear from FIG. 12, the amount of top board sagging of the top board 31 is the greatest at the top board position 313, and the amount of top board sagging of the top board 31 is the smallest at the top board position 311. Also, at a capturing distance C which is a capturing range farthest from the fulcrum 0, the difference in the amount of top board sagging is significant.

The top board sagging amount estimation unit 464 (FIG. 9) estimates the amount of top board sagging (the amount of sagging), and then, stores the estimated amount of top board sagging in the correction data storage unit 45. Additionally, this estimated amount of top board sagging may be treated as a part of the amount of correction for top board sagging.

The alignment adjustment unit 465 (FIG. 9) estimates the inclination of the top board 31 based on the amount of top board sagging (the amount of sagging) estimated by the top board sagging amount estimation unit 464, and performs alignment for each captured image of the object P.

As described above, according to the present embodiment, the PET-CT device 100 estimates, by the correction unit 46, the weight distribution of the object P on the top board 31 from a scanogram at the time of capturing an X-ray CT image, and estimates the amount of top board sagging of the top board 31 from the weight distribution.

The PET-CT device 100 may thereby perform alignment of the PET image and the X-ray CT image respectively based on the estimated amount of top board sagging. Additionally, the PET image used for alignment is the PET image on which attenuation correction has been performed by the PET reconstruction unit 44 and which is stored in the correction data storage unit 45.

As described above, the PET-CT device 100 according to the present embodiment is capable of estimating the amount of top board sagging of the top board 31 from a scanogram in which the top board 31 is not shown, and thus, an X-ray CT image showing the top board 31 is not necessary, and also, a captured image may be corrected without actually measuring the amount of top board sagging of the top board 31.

Next, an overall procedure of image processing by the PET-CT device 100 according to the present embodiment will be described.

Figure 13:
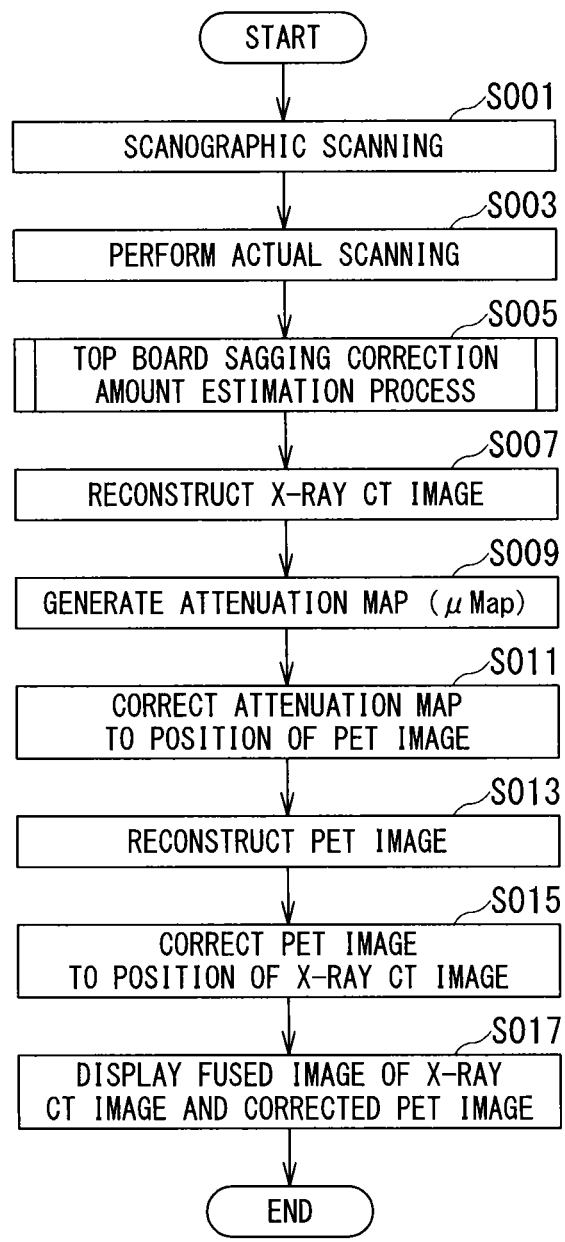
FIG. 13 is a flow chart showing an overall procedure of image processing by the PET-CT device according to the present embodiment.

FIG. 13 is a flow chart showing an overall procedure of image processing by the PET-CT device 100 according to the present embodiment.

First, the CT gantry device 2 of the PET-CT device 100 according to the present embodiment performs scanographic scanning on the object P lying on the top board 31 to acquire a scanogram (step S001). The CT gantry device 2 captures the object P by the helical scanning method, and then, stores the X-ray projection data for generating a scanogram in the X-ray projection data storage unit 41.

Next, the PET-CT device 100 performs actual scanning (step S003). Specifically, the CT gantry device 2 radiates X-rays on the object P lying on the top board 31 by the helical scanning method, and generates the X-ray projection data for reconstructing an X-ray CT image. Also, the PET gantry device 1 detects gamma rays with respect to the object P lying on the top board 31 by the step-and-shoot method, and generates the gamma-ray projection data for reconstructing a PET image.

Next, the correction unit 46 of the console device 4 performs a top board sagging correction amount estimation process for performing alignment of a PET image generated by the PET gantry device 1 (step S005). The correction unit 46 estimates the amount of correction for top board sagging (the amount of top board sagging of the top board 31 and the inclination of the top board 31) by the top board sagging correction amount estimation process, and stores the same in the correction unit 46.

Next, the CT image reconstruction unit 42 reconstructs the X-ray CT image using the X-ray projection data stored in the X-ray projection data storage unit 41 (step S007). Then, the CT image reconstruction unit 42 stores the reconstructed X-ray CT image in the correction data storage unit 45, and also, transmits the same to the attenuation map generation unit 50.

Next, the attenuation map generation unit 50 generates an attenuation map (μ Map) for correcting the attenuation of gamma rays using the X-ray CT image reconstructed by the CT image reconstruction unit 42 (step S009).

Next, the attenuation map generation unit 50 corrects the attenuation map to the position of the PET image such that the height of the top board will be the same as in the PET image (step S011), based on the amount of correction for top board sagging (the amount of top board sagging of the top board 31 and the inclination of the top board 31) stored in the correction data storage unit 45, and stores the corrected attenuation map in the correction data storage unit 45.

Next, the PET reconstruction unit 44 reconstructs the PET image using the gamma-ray projection data stored in the gamma-ray projection data storage unit 43 (step S013). In this case, the PET reconstruction unit 44 reads the attenuation map from the correction data storage unit 45, and performs reconstruction (attenuation correction) of the PET image using the attenuation map which has been read out and the gamma-ray projection data. Then, the PET reconstruction unit 44 stores the reconstructed PET image in the correction data storage unit 45.

Next, the correction unit 46 reads the attenuation-corrected PET image and the X-ray CT image from the correction data storage unit 45, and corrects the PET image to the position of the X-ray CT image by the alignment adjustment unit 465 (step S015). Then, the correction unit 46 fuses the X-ray CT image and the corrected PET image, and stores the fused image in the correction data storage unit 45.

Then, the control unit 47 reads the fused image stored in the correction data storage unit 45, and causes the fused image of the X-ray CT image and the corrected PET image to be displayed on a display unit, not shown, of the console device 4 (step S017).

As described above, the PET-CT device 100 according to the present embodiment generates a fused image by aligning the X-ray CT image and the PET image by the correction unit 46, causes the generated fused image to be displayed on a display unit, and ends the process. The operation of the correction unit 46 will now be described in detail.

Figure 14:
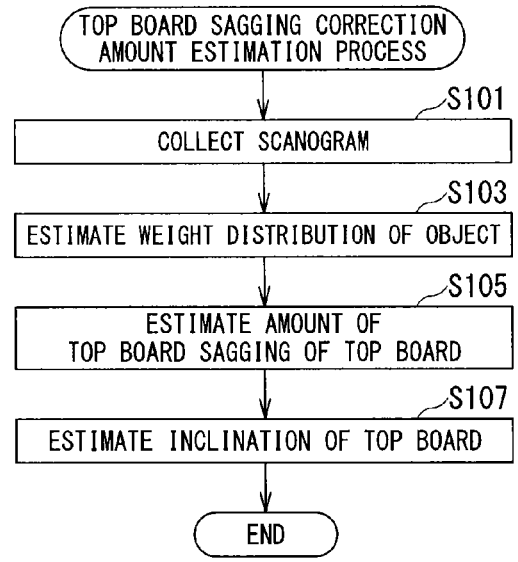
FIG. 14 is a flow chart showing a procedure of a top board sagging correction amount estimation process for estimating the amount of correction for top board sagging by the correction unit (FIG. 9) of the PET-CT device according to the present embodiment.

FIG. 14 is a flow chart showing a procedure of the top board sagging correction amount estimation process for estimating the amount of correction for top board sagging by the correction unit 46 (FIG. 9) of the PET-CT device 100 according to the present embodiment.

As shown in FIG. 14, the image collection unit 461 (FIG. 9) of the correction unit 46 collects a scanogram of the object P from the correction data storage unit 45 (step S101).

Next, the weight distribution estimation unit 462 (FIG. 9) estimates the weight distribution of the object P from the scanogram collected by the image collection unit 461 (step S103). Additionally, the weight distribution estimation unit 462 may estimate the weight distribution for each body axis by calculating a luminance value integral obtained by integrating the luminance values of a collected scanogram and calculating the water equivalent thickness, or may estimate the weight distribution of the object P by calculating a water equivalent thickness profile from the scanogram and the water phantom, for example.

Next, the top board sagging amount estimation unit 464 (FIG. 9) estimates the amount of top board sagging of the top board 31 on which the object P is placed, from the weight distribution of the object P estimated by the weight distribution estimation unit 462 (step S105). The top board sagging amount estimation unit 464 may use any calculation method to estimate the amount of top board sagging, and for example, it is possible to use the method of calculating the "amount of bending in a beam", which is a known art, and estimate the amount of top board sagging of the top board 31 from the distance between the fulcrum of the top board 31 and a capturing position, the position of a support portion, the weight position, the weight distribution or the like.

Next, the alignment adjustment unit 465 (FIG. 9) estimates the inclination of the top board 31 based on the amount of top board sagging of the top board 31 estimated by the top board sagging amount estimation unit 464 (step S107), and stores the amount of top board sagging of the top board 31 and the inclination of the top board 31 in the correction data storage unit 45.

The alignment adjustment unit 465 may thereby align, as indicated by step S015 (FIG. 13), the X-ray CT image captured in the actual scanning by the CT gantry device 2 by the helical scanning method and the PET image after attenuation correction, and perform alignment based on the amount of correction for top board sagging (the amount of top board sagging of the top board 31 and the inclination of the top board 31).

As described above, according to the present embodiment, the PET-CT device 100 calculates, by the correction unit 46, the weight distribution of the object P on the top board 31 from the scanogram image (positioning image) at the time of capturing the X-ray CT image, and estimates the amount of top board sagging of the top board 31 from the weight distribution.

The PET-CT device 100 according to the present embodiment may thereby perform alignment of the captured PET image and the X-ray CT image based on the estimated amount of top board sagging of the top board 31, and thus, alignment of the top board 31 may be appropriately performed, and highly accurate correction with the fused PET image and X-ray CT image may be performed and a fused image may be obtained.

As described above, the PET-CT device 100 according to the present embodiment is capable of estimating the amount of top board sagging of the top board 31 from a scanogram in which the top board 31 is not shown, and thus, an X-ray CT image showing the top board 31 is not necessary, and also, a captured image may be corrected without actually measuring the amount of top board sagging of the top board 31.

Second Embodiment

According to the first embodiment described above, the weight distribution estimation unit 462 estimates' the weight distribution of the object P by calculating the luminance value integral or the water equivalent thickness profile, and the top board sagging amount estimation unit 464 estimated the amount of top board sagging of the top board 31 at the time of actual scanning, based on the estimated weight distribution.

According to a second embodiment, the correction unit 46 according to the first embodiment further includes a center-of-gravity estimation unit 463, and the amount of top board sagging of the top board 31 that takes into account the position of the center of gravity at the time of the weight of the object P being applied to the top board 31 is corrected.

Figure 15:
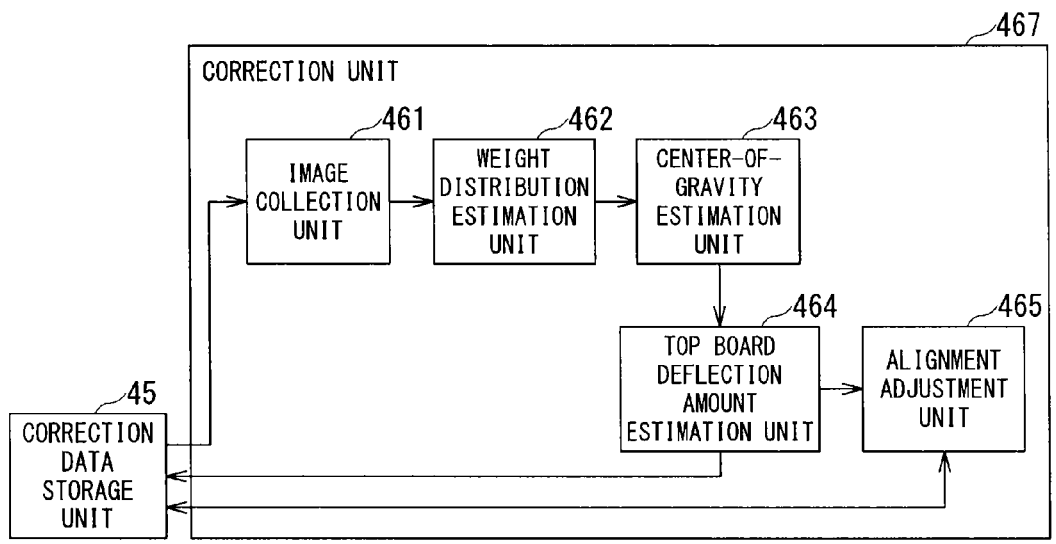
FIG. 15 is a functional block diagram showing a configuration of a correction unit of a console device of a PET-CT device according to a second embodiment.

FIG. 15 is a functional block diagram showing a configuration of a correction unit 467 of the console device 4 of the PET-CT device 100 according to the second embodiment.

As shown in FIG. 15, the correction unit 467 according to the second embodiment is configured by further providing the center-of-gravity estimation unit 463 to the correction unit 46 according to the first embodiment. Additionally, the same elements will be denoted with the same reference signs, and description thereof will be omitted.

The center-of-gravity estimation unit 463 estimates the position of the center of gravity of the object P from the weight distribution estimated by the weight distribution estimation unit 462.

First, the weight distribution estimation unit 462 calculates a luminance value integral by integrating the luminance values in the body axis direction of the object P shown in FIG. 10, for example. Then, the center-of-gravity estimation unit 463 estimates the center of gravity of the object P from the AUC of a luminance value integral profile for each body axis position estimated by the weight distribution estimation unit 462. Additionally, the luminance value integral profile is an analysis result or analysis information for estimating the body weight constituted from the luminance value integral. The position of the center of gravity and the concept of the distance from a fulcrum 0 are shown in the drawing.

Figure 16:
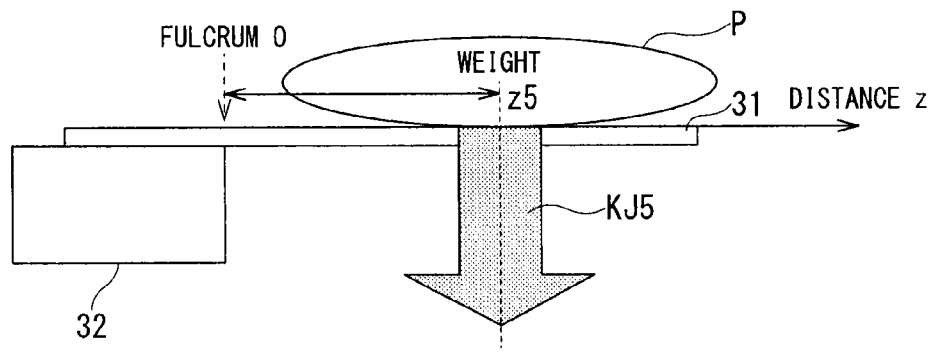
FIG. 16 is an explanatory diagram for describing the concept of estimation of the position of the center of gravity of an object by a center-of-gravity estimation unit according to the second embodiment.

FIG. 16 is an explanatory diagram for describing the concept of estimation of the position of the center of gravity of the object P by the center-of-gravity estimation unit 463 according to the present embodiment.

As shown in FIG. 16, the concept of application of the weight of the object P on the top board 31 is shown using weight KJ5, based on the AUC of the luminance value integral profile.

The center-of-gravity estimation unit 463 estimates the position of the center of gravity where the weight KJ5 of the object P is applied on the top board 31 from the luminance value integral profile, and then converts the estimated position of the center of gravity to the distance from the fulcrum 0 of the top board 31 to the position of the center of gravity, and estimates a distance z5 from the fulcrum 0 of the top board 31 to the position of the center of gravity.

In this case, the top board sagging amount estimation unit 464 multiplies the weight KJ5 estimated from the luminance value integral profile and the distance z5 from the fulcrum 0 of the top board 31 to the position of the center of gravity, and calculates a moment Mw. This moment Mw is a unique value obtained by multiplying a distance (z) from the fulcrum 0 of the top board 31 and weight (w).

Then, the top board sagging amount estimation unit 464 refers to a database of the amount of top board sagging stored in the correction data storage unit 45, and estimates the amount of top board sagging at the distance z5. The database of the amount of top board sagging will now be described.

Figure 17:
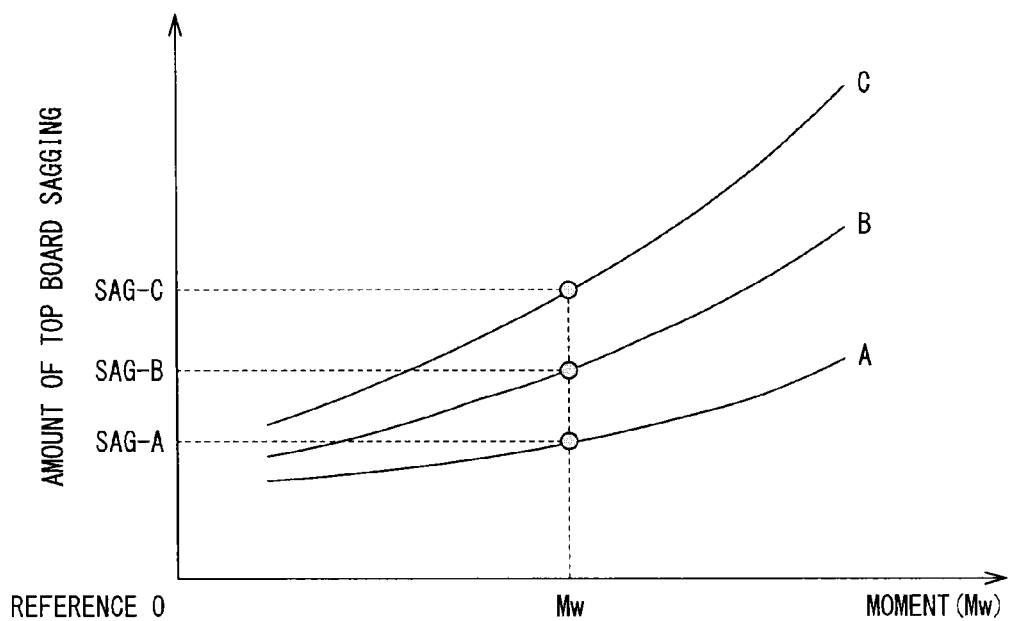
FIG. 17 is an explanatory diagram showing a relative relationship between a moment and the amount of top board sagging according to the second embodiment.

FIG. 17 is an explanatory diagram showing a relative relationship (referred to also as a curve of the amount of top board sagging) between the moment Mw and the amount of top board sagging according to the second embodiment.

As shown in FIG. 17, the top board sagging amount estimation unit 464 estimates the amount of top board sagging at points A, B and C (see FIG. 12) indicating the distances from the fulcrum 0 of the top board 31, by calculating the moment Mw.

Specifically, the top board sagging amount estimation unit 464 calculates the moment Mw at a certain distance z5, and refers to the curve of the amount of top board sagging corresponding to the moment Mw. As shown in FIG. 17, the amount of top board sagging at point A on the top board 31 corresponding to the moment Mw is estimated to be SAG-A, the amount of top board sagging at point B on the top board 31 is estimated to be SAG-B, and the amount of top board sagging at point C on the top board 31 is estimated to be SAG-C. According to the second embodiment, the relative relationship between the moment Mw and the amount of top board sagging is shown by the curve of the amount of top board sagging, and is stored in the correction data storage unit 45 as the database of the amount of top board sagging.

As described above, this curve of the amount of top board sagging is a table for estimating the amount of top board sagging at a point at a predetermined distance from the fulcrum 0 of the top board 31 by calculating the moment Mw at an arbitrary distance.

Additionally, in the present embodiment, the curve of the amount of top board sagging is stored in the correction data storage unit 45 as a table in which the amount of top board sagging is compiled as a database, but the present embodiment is not restricted to be such, and the method of calculating the "amount of bending in a beam", which is a known art, mentioned in the first embodiment may also be applied.

Next, an operation of the correction unit 467 according to the second embodiment will be described.

Figure 18:
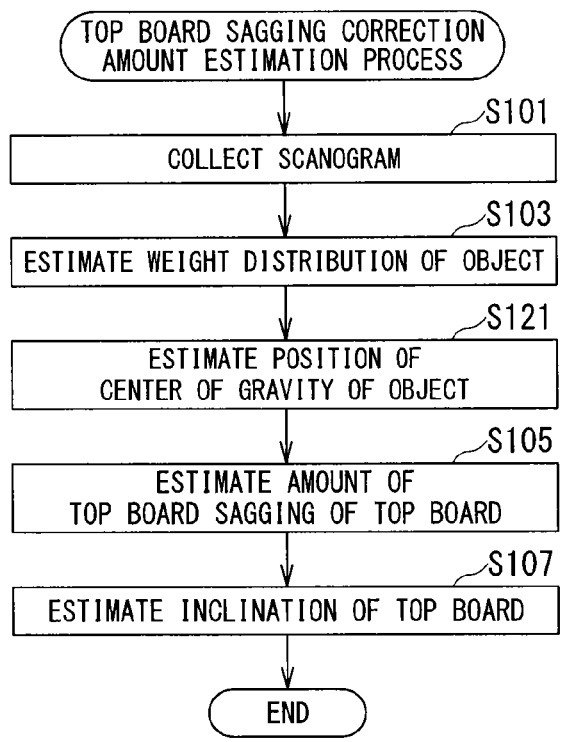
FIG. 18 is a flow chart showing a procedure of a top board sagging correction amount estimation process for estimating the amount of correction for top board sagging by the correction unit (FIG. 15) of the PET-CT device according to the second embodiment.

FIG. 18 is a flow chart showing a procedure of a top board sagging correction amount estimation process for estimating the amount of correction for top board sagging by the correction unit 467 (FIG. 15) of the PET-CT device 100 according to the second embodiment. Additionally, steps of the same processing as in the flow chart shown in FIG. 14 will be denoted with the same reference numerals, and description thereof will be omitted.

The flow chart of FIG. 18 according to the second embodiment is different from the flow chart of FIG. 14 according to the first embodiment in that step S121 is added. That is, the center-of-gravity estimation unit 463 (FIG. 15) estimates the position of the center of gravity of the object P from the weight distribution estimated by the weight distribution estimation unit 462 (step S121).

The top board sagging amount estimation unit 464 estimates, based on the position of the center of gravity of the object P estimated by the center-of-gravity estimation unit 463, the amount of top board sagging of the top board 31 by referring to the curve of the amount of top board sagging (FIG. 17) or by using the method for calculating the "amount of bending in a beam", which is a known art, for example.

As described above, according to the second embodiment, the PET-CT device 100 calculates, by the correction unit 467, the weight distribution of the object P on the top board 31 from a scanogram image (a positioning image) at the time of capturing an X-ray CT image, then estimates the position of the center of gravity, and estimates the amount of top board sagging of the top board 31 from the weight applied at the estimated position of the center of gravity.

The PET-CT device 100 according to the present embodiment may thereby perform alignment of the captured PET image and the X-ray CT image based on the estimated amount of top board sagging of the top board 31, and thus, alignment of the top board 31 may be appropriately performed, and highly accurate correction with the fused PET image and X-ray CT image may be performed and a fused image may be obtained.

Additionally, in the first and second embodiments described above, the PET-CT device 100 generates a PET image using the PET gantry device 1, but a single photon emission computed tomography device (SPECT device) may be alternatively used, for example.

Third Embodiment

According to the first and second embodiments described above, the top board sagging amount estimation unit 464 estimates the amount of top board sagging of the top board 31 using a scanogram, and the alignment adjustment unit 465 aligns the PET image and the X-ray CT image based on the amount of top board sagging to thereby generate a fused image.

In a third embodiment, a mode is described where the PET-CT device 100 causes the CT gantry device 2, instead of the PET gantry device 1, to successively capture the object P by the step-and-shoot method, and the amount of top board sagging based on the weight distribution estimated from a scanogram is used in the alignment of the successively captured X-ray CT images.

Specifically, the top board sagging amount estimation unit 464 estimates the amount of top board sagging of the top board 31 based on the weight distribution estimated from a scanogram, and estimates the same to be the amount of top board sagging of the top board 31 in a scan region of an X-ray CT image captured by the step-and-shoot method. Then, the alignment adjustment unit 465 performs alignment on the volume data of the actual scanning successively captured by the CT gantry device 2 by the step-and-shoot method in such a way that the top board positions are aligned.

Figure 19:
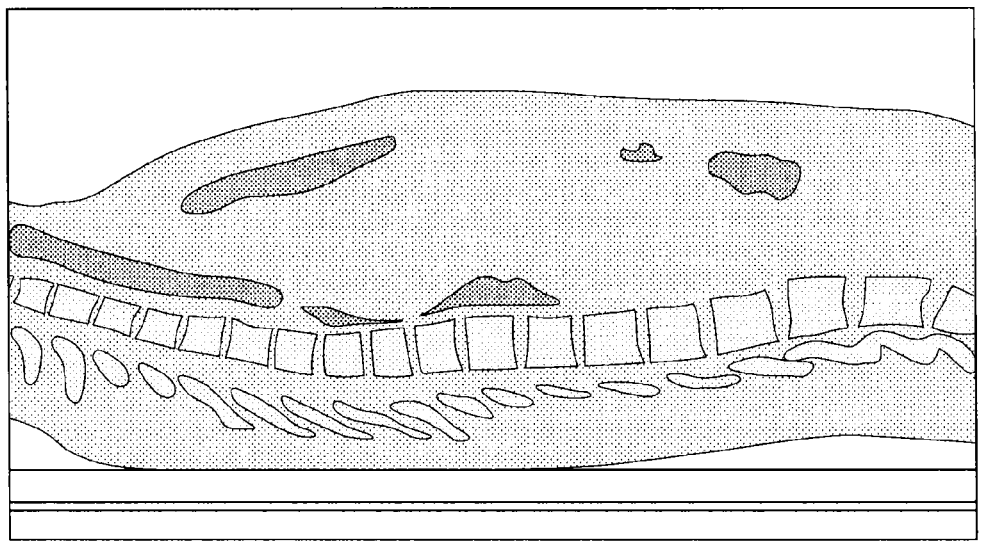
FIG. 19 is an example display of an X-ray CT image where an alignment adjustment unit according to a third embodiment has performed alignment in such a way that top board positions of volume data are aligned.

FIG. 19 is an example display of an X-ray CT image where the alignment adjustment unit 465 according to the third embodiment has performed alignment in such a way that the top board positions of the volume data are aligned. Additionally, the volume data is an image of a cross section of a human body obtained from the X-ray CT image, and is a diagram showing the distribution of concentration or density in the space.

As shown in FIG. 19, even if the X-ray CT images are captured successively by the step-and-shoot method, the PET-CT device 100 may estimate the amount of top board sagging of the top board 31 based on the weight distribution estimated from a scanogram, by the top board sagging amount estimation unit 464, and estimate the amount of top board sagging in a scan region of the X-ray CT image.

The PET-CT device 100 according to the third embodiment may thereby appropriately perform alignment, by the alignment adjustment unit 465, of the volume data of the X-ray CT images successively captured by the step-and-shoot method, based on the amount of top board sagging estimated by the top board sagging amount estimation unit 464.

According to the first to third embodiments described above, the amount of top board sagging of the top board may be estimated using a scanogram at the time of capturing the X-ray CT image by the helical scanning method, and thus, by correcting the estimated amount of top board sagging to be the amount of top board sagging at the time of performing capturing by another capturing method, it becomes possible not to restrict the capturing method at the time of performing capturing.

Fourth Embodiment

According to the first to third embodiment described above, the image collection unit 461 collects a scanogram of the object P, and the weight distribution estimation unit 462 calculates the luminance value integral or the water equivalent thickness from the collected scanogram, and estimates the weight distribution of the object P.

In the fourth embodiment, the weight distribution estimation unit 462 estimates the weight distribution of the object P by estimating a scanogram including a part not scanned or a luminance value integral or the water equivalent thickness not calculated.

Specifically, the weight distribution estimation unit 462 estimates the body shape of the object P from the collected scanogram, and estimates that the head is at a position 30 cm above the position of the shoulders in the body axis direction, or that the ankle is at a position 1.2 m below the position of the lungs in the body axis direction, for example. Also, the weight distribution estimation unit 462 may refer to the patient information of the object P, and estimate the body shape of the object P from the average height based on the height, the weight or age.

As described, the weight distribution estimation unit 462 estimates the body shape or a part corresponding to a scanogram that is not collected, to thereby generate a scanogram that is not reconstructed, and to estimate the weight distribution of the object P based on the generated scanogram.

Also, the weight distribution estimation unit 462 may estimate the water equivalent thickness which is not yet calculated or the luminance value integral of the object P to estimate the weight distribution of the object.

For example, since the density of tissues is indicated by the luminance value integral, the weight distribution estimation unit 462 may estimate the body shape and obtain the luminance value integral from the body shape to thereby estimate the weight distribution of the object P. Also, in the case of the water equivalent thickness, since the body thickness is calculated from the scanogram and the water phantom, the weight distribution estimation unit 462 may estimate the body shape and calculate the water equivalent thickness from the estimated body shape to thereby estimate the weight distribution of the object P.

Additionally, the PET-CT device 100 is capable of automatically determining, by the couch 32, the position of the head or the position of the legs, and thus, the position of the head or the position of the legs may be automatically set based on the collected scanogram.

Although a couple of embodiments of the invention are explained, these embodiments are exemplary only and it is not intended that the scope of the invention is limited by the embodiments. These embodiments can be put into practice in other various forms, and can be variously omitted, replaced or changed within the scope of the invention. The embodiments and their modifications are included in the scope and the coverage of the invention, and similarly in the equivalents to the claimed invention.

Also, in the embodiments of the present invention, the steps of flow charts show example processes that are performed in time-series in the order described, but they may also include processes that can be performed in parallel or independently rather than being performed in time-series.

What is claimed is:

1. An image diagnosis device, comprising:
   processing circuitry configured to collect a positioning image for an object;
   estimate a weight distribution of the object from the collected positioning image, wherein the processing circuitry is further configured to calculate a water equivalent thickness profile obtained by estimating a water equivalent thickness of each body axis position of the object, based on the collected positioning image, and estimate the weight distribution based on the water equivalent thickness profile;
   estimate an amount of sagging of a top board on which the object is placed, from the estimated weight distribution; and
   perform alignment for each captured image of the object, based on the estimated amount of sagging of the top board.

2. The image diagnosis device according to claim 1, wherein the processing circuitry is further configured to estimate a weight distribution in a case where weight of the object is distributed over a plurality of points on the top board, and
   wherein the processing circuitry is further configured to estimate the amount of sagging of the top board based on the estimated weight distribution over the plurality of points and a distance from a fulcrum of the top board to a weight position in the weight distribution.

3. The image diagnosis device according to claim 1, wherein the processing circuitry is further configured to
   estimate a position of a center of gravity of the object from the estimated weight distribution, and
   estimate the amount of sagging of the top board based on the estimated position of the center of gravity and weight applied at the position of the center of gravity.

4. The image diagnosis device according to claim 3, further comprising:
   a table used to estimate the amount of sagging of the top board based on a distance from the fulcrum of the top board to a weight position and weight applied at the weight position,
   wherein the processing circuitry is further configured to convert the estimated position of the center of gravity to a distance from the fulcrum of the top board to a weight position, and estimate the amount of sagging of the top board using the table, based on the distance from the fulcrum of the top board to the weight position obtained by the conversion and weight applied at the position of the center of gravity.

5. The image diagnosis device according to claim 1, wherein the processing circuitry is further configured to calculate, for the collected positioning image, a luminance value integral by integrating luminance values indicating luminance at each body axis position, and estimate the weight distribution based on the luminance value integral.

6. The image diagnosis device according to claim 1, wherein the processing circuitry is further configured to estimate an inclination of the top board at a corresponding capturing position from the estimated amount of sagging of the top board, and perform alignment with respect to the inclination of the top board for each captured image of the object.

7. The image diagnosis device according to claim 1, wherein the processing circuitry is further configured to perform alignment between an X-ray CT image captured by a helical scanning method and a PET image captured by a step-and-shoot method.

8. The image diagnosis device according to claim 1, wherein the processing circuitry is further configured to perform alignment of the top board for each piece of volume data of X-ray CT images obtained by successively capturing the object by the step-and-shoot method.

9. The image diagnosis device according to claim 1, wherein the processing circuitry is further configured to estimate a body shape of the object based on the collected positioning image, and estimate the weight distribution of the object based on the estimated body shape.

10. A control method of an image diagnosis device, the method comprising:
    collecting a positioning image for an object;
    estimating a weight distribution of the object from the collected positioning image;
    estimating an amount of sagging of a top board on which the object is placed, from the estimated weight distribution; and
    performing alignment for each captured image of the object, based on the estimated amount of sagging of the top board, wherein the estimating step further comprises calculating a water equivalent thickness profile obtained by estimating a water equivalent thickness of each body axis position of the object, based on the collected positioning image, and estimate the weight distribution based on the water equivalent thickness profile.

* * * * *